United States Patent [19]

Müller et al.

[11] Patent Number: 4,675,425

[45] Date of Patent: Jun. 23, 1987

[54] METHOD FOR PREPARING ORGANOSILYL CARBONATES

[75] Inventors: Johann Müller; Christa Trieschmann; Walter Doskocil; Gerhard Preiner, all of Burghausen, Fed. Rep. of Germany

[73] Assignee: Wacker Chemie GmbH, Munich, Fed. Rep. of Germany

[21] Appl. No.: 801,185

[22] Filed: Nov. 25, 1985

[30] Foreign Application Priority Data

Aug. 3, 1985 [DE] Fed. Rep. of Germany ....... 3508363

[51] Int. Cl.$^4$ ............................. C07F 7/08; C07F 7/18
[52] U.S. Cl. ...................................... 556/442
[58] Field of Search ........................................ 556/442

[56] References Cited

U.S. PATENT DOCUMENTS 2,566,347  9/1951  MacKenzie ......................... 556/442

OTHER PUBLICATIONS

W. C. Butts and W. T. Rainey, Jr., "Gas Chromatography and Mass Spectrometry of the Trimethylsilyl Derivatives of Inorganic Anions", *Analytical Chemistry*, vol. 43, No. 4, (Apr. 1971), pp. 538–541.

Y. Yamamoto and D. S. Tarbell, "The Preparation and Reaction of tert-Butyl Trimethylsilyl Carbonate and Related Compounds", *Journal of Organic Chemistry*, vol. 36, No. 20, (1971), pp. 2954–2956.

Walter Noll, Chemistry and *Tecknology of Silicones*, 2nd German Edition, New York: Academic Press, (1982), p. 168.

Walter Noll, "Chemie and Technologie der Silicone", Weinheim, (1968), p. 168.

*Primary Examiner*—Paul F. Shaver

[57] ABSTRACT

Organosilyl carbonates, such as bis(trimethylsilyl)carbonate, are prepared by reacting an organohalosilane with an alkali bicarbonate in the presence of an amine and/or a phosphine and an aprotic solvent, preferably a polar solvent which is inert to the reactants. The resultant mixture is separated from the ammonium halide and/or phosphonium halide and the organosilyl carbonate is recovered from the halide-free mixture.

9 Claims, No Drawings

METHOD FOR PREPARING ORGANOSILYL CARBONATES

The present invention relates to organosilyl carbonates, particularly to a method for preparing organosilyl carbonates and more particularly to a method for preparing bis(triorganosilyl)carbonates.

BACKGROUND OF THE INVENTION

Organosilyl carbonates are well known and methods for preparing organosilyl carbonates are described by W. C. Butts et al in Analytical Chemistry, Vol. 43, No. 4, 1971, pages 538 to 542 and Y. Yamamoto et al in Journal of Organic Chemistry, Vol. 36, No. 20, 1971, pages 2954 to 2956.

It is an object of the present invention to provide a method for preparing organosilyl carbonates. Another object of the present invention is to provide a method for preparing organosilyl carbonates from readily available materials. Still another object of the present invention is to provide a method for preparing organosilyl carbonates on a large scale. A further object of the present invention is to provide a method for preparing bis(triorganosilyl)carbonates.

SUMMARY OF THE INVENTION

The foregoing objects and others which will become apparent from the following description are accomplished in accordance with this invention, generally speaking, by providing a method for preparing organosilyl carbonates which comprises reacting an organohalosilane with an alkali bicarbonate in the presence of an amine and/or phosphine and an inert aprotic solvent, removing the ammonium halide and/or phosphonium halide from the mixture and thereafter recovering the organosilyl carbonate.

DESCRIPTION OF THE INVENTION

The organohalosilane used in the method of this invention preferably has the formula

$$R_aSiX_{4-a}$$

in which R represents the same or different monovalent SiC-bonded organic radicals, X represents the same or different halogen atoms and a represents 1, 2 or 3, preferably 3.

The halogen atoms represented by X in the above formula can be fluorine, chlorine, bromine or iodine. However, X is preferably chlorine because of its availability.

Examples of monovalent SiC-bonded organic radicals represented by R include hydrocarbon radicals having from 1 to 18 carbon atoms per radical such as alkyl radicals, for example, methyl, ethyl, n-propyl, n-butyl, sec-butyl and octadecyl radicals; cycloalkyl radicals such as the cyclohexyl radical; hydrocarbon radicals having 2 to 18 carbon atoms per radical and containing aliphatic carbon-carbon multiple bonds, such as ethynyl, vinyl, allyl, methallyl and styryl radicals; aryl radicals, such as the phenyl radical; alkaryl radicals such as the tolyl radical; and aralkyl radicals such as the benzyl radical.

These hydrocarbon radicals may contain substituents which are inert with respect to the Si-bonded halogen and alkali bicarbonates. Examples of such substituted hydrocarbon radicals include halogenated monovalent hydrocarbon radicals such as 3-chloropropyl, 3,3,3-trifluoropropyl, o-, p- and m-chlorophenyl and bromotolyl radicals; monovalent aliphatic radicals consisting of carbon, hydrogen, ether oxygen and fluorine atom(s) such as 1,1,2,2,3,3-hexafluoropropyloxypropyl and 1,1,2,2-tetrafluoroethoxypropyl radicals; and monovalent hydrocarbon radicals substituted only by ether oxygen such as the p-methoxyphenyl radical.

The preferred organohalosilanes employed in the method of this invention are trimethylchlorosilane and vinyldimethylchlorosilane.

In the method of this invention, amine or phosphine compounds or amine and phosphine compounds are employed to combine with the hydrogen halide to form ammonium halides or phosphonium halides. In the absence of the amine or phosphine compounds, triorganosilanol and/or hexaorganodisiloxane is the only organosilicon compound formed from the reaction of triorganohalosilanes and sodium bicarbonate (cf. W. Noll, "Chemie und Technologie der Silicone", Weinheim, 1968, page 168).

The preferred alkali bicarbonate is sodium bicarbonate because of its availability; however, potassium bicarbonate or lithium bicarbonate, for example, can also be used.

The alkali bicarbonate is preferably employed in the method of this invention in an amount of at least 1 mol per gram atom of Si-bonded halogen, and more preferably in an amount of from 3 to 5 mols per gram-atom of Si-bonded halogen.

Any amine or phosphine compound can be used which will combine with hydrogen halide, and especially hydrogen chloride, to form ammonium halides or phosphonium halides. It is preferred that amines be employed rather than phosphines in the method of this invention because of the limited toxicity of the amines.

Examples of preferred amines are those which are liquid at room temperature and have a boiling point of at most 50° C. at 150 hPa (absolute), such as hexamethyldisilazane and triethylamine. Other examples of amines that can be used in the method of this invention are cyclohexylamine, piperidine, pyridine, chloroethyldimethylamine and n-butylamine.

A preferred phosphine which may be employed in the method of this invention is tri-n-butylphosphine.

Amines and/or phosphines are preferably employed in the method of this invention in an amount of at least 1 mol per gram-atom of Si-bonded halogen, and more preferably in an amount of from 3 to 5 mols per gram-atom of Si-bonded halogen.

The preferred aprotic solvents, which are inert with respect to the reactants, are polar solvents having a boiling point of at most 50° C. at 150 hPa (absolute). Examples of suitable polar solvents are polar halohydrocarbons, such as dichloromethane, or ethers, such as diethyl ether. Dichloromethane is the preferred solvent in which to conduct the reaction of the organohalosilane with the alkali bicarbonate and amine and/or phosphine because of its ease of handling.

The aprotic solvent which is inert with respect to the reactants is preferably used in an amount of from 100 to 1200 percent based on the weight of the organohalosilane.

The organohalosilane is reacted with the alkali bicarbonate and amine and/or phosphine by or during mixing of the reactants. This is preferably run at 10° to 50° C. and at atmospheric pressure, i.e., at 1020 hPa (absolute) or about 1020 hPa (absolute).

The ammonium halide or phosphonium halide is separated from the mixture obtained by reacting the organohalosilane with the alkali bicarbonate in the presence of an amine and/or phosphine, and an aprotic solvent which is inert with respect to the reactants, by mixing the mixture with an aprotic nonpolar solvent that is inert with respect to the reaction products in order to form a precipitate of ammonium halide and/or phosphonium halide. The precipitated ammonium halide and/or phosphonium halide is filtered, decanted or centrifuged from the mixture. Hydrocarbons having a boiling point of at most 50° C. at 150 hPa (absolute), especially n-hexane, are preferred as the nonpolar solvent.

The nonpolar solvent is preferably used in an amount of from 100 to 1000 weight percent, based on the weight of the organohalosilane employed to produce the desired organosilyl carbonate.

Separation of the ammonium halide and/or phosphonium halide from the mixture obtained by the reaction of the organohalosilane with the alkali bicarbonate in the presence of an amine and/or phosphine and an aprotic solvent which is inert with respect to the reactants, is preferably performed at 10° to 50° C. at atmospheric pressure, i.e., at 1020 hPa (absolute) or about 1020 hPa (absolute).

To isolate the desired organosilyl carbonate, especially organosilyl carbonates having the formula

R$_3$SiOCOOSiR$_3$ in which R is the same as above, the solvent, excess amine and/or phosphine and other substances which have a boiling point below that of the desired organosilyl carbonate are preferably evaporated off at or below 50° C. and at or below 150 hPa (abso- lute).

It is preferred that the method of this invention be conducted under anhydrous conditions or under conditions from which water is excluded to the extent possible.

The organosilyl carbonates produced according to this invention can be used, for example, for treating pyrogenic silicon dioxide to render it hydrophobic or for the silylation Chemistry, Vol. 38, No. 14, 1973, pages 2521 to 2525)

EXAMPLE 1

(a) A solution containing 43.6 g of trimethylchlorosilane in 40 g of dichloromethane (purity: at least 99.5 weight percent CH$_2$Cl$_2$) is introduced dropwise over 30 minutes with stirring and with the exclusion of water into a flask equipped with an agitator, an addition funnel, thermometer and reflux condenser and containing a mixture consisting of 134 g of sodium bicarbonate (purity: at least 99.5 weight percent NaHCO$_3$), 162 g of anhydrous triethylamine and 100 g of dichloromethane (purity: at least 99.5 weight percent CH$_2$Cl$_2$). The temperature of the contents of the flask rises to about 40° C. After the addition of the silane in the aprotic solvent has been completed, stirring is continued for an additional 2 hours, during which time the contents of the flask cool to room temperature. The organosilicon compounds present in a sample obtained from the resultant mixture consist of 81 mol percent of bis(trimethylsilyl)carbonate and 19 mol percent of hexamethyldisiloxane according to the $^1$H-NMR spectrum.

(b) The mixture prepared in accordance with the procedure described in (a) above is mixed with 1000 g of anhydrous n-hexane and filtered under an atmosphere of dry nitrogen. The substances boiling below bis(trimethylsilyl)carbonate are distilled from the filtrate at room temperature and at 10 hPa (absolute). About 56.6 g of bis(trimethylsilyl)carbonate is recovered as the residue.

EXAMPLE 2

(a) A solution containing 4.4 g of trimethylchlorosilane in 5 g of dichloromethane (purity: at least 99.5 weight percent CH$_2$Cl$_2$) is added dropwise over a period of 5 minutes with stirring and exclusion of water to a flask equipped with an agitator, an addition funnel, thermometer and reflux condenser and containing a mixture consisting of 11.9 g of potassium bicarbonate (purity: at least 99.5 weight percent of KHCO$_3$), 16.2 g of anhydrous triethylamine and 10 g of dichloromethane (purity: at least 99.5 weight percent CH$_2$Cl$_2$). The contents of the flask increases to a temperature of about 30° C. After the addition of the silane in the aprotic solvent is complete, stirring is then continued for an additional 2 hours, during which time the contents of the flask cool to room temperature. The organosilicon compounds present in a sample of the resultant mixture consist of 65 mol percent of bis(trimethylsilyl)carbonate and 35 mol percent of hexamethyldisiloxane according to the $^1$H-NMR spectrum.

(b) The mixture prepared in accordance with the procedure described in (a) above is mixed with 200 g of anhydrous n-hexane and filtered under dry nitrogen. The substances boiling below bis(trimethylsilyl)carbonate are distilled from the filtrate at room temperature and at 10 hPa (absolute). About 3.3 g of bis(trimethylsilyl)carbonate is recovered as the residue.

EXAMPLE 3

(a) A solution containing 24.1 g of vinyldimethylchlorosilane in 24 g of dichloromethane (purity: at least 99.5 weight percent CH$_2$Cl$_2$) is added dropwise over 15 minutes with stirring and with the exclusion of water to a flask equipped with an agitator, an addition funnel, thermometer and reflux condenser and containing a mixture consisting of 67.2 g sodium bicarbonate (purity: at least 99.5 weight percent NaHCO$_3$), 162 g of anhydrous triethylamine and 100 g of dichloromethane (purity: at least 99.5 weight percent CH$_2$Cl$_2$). After the addition of the silane in the aprotic solvent is complete, stirring is continued for an additional 3.5 hours. The organosilicon compounds present in a sample of the resultant mixture consist of 55 mol percent of bis(vinyldimethylsilyl)carbonate and 45 mol percent of 1,3-divinyl-1,1,3,3-tetramethyldisiloxane according to the $^1$H-NMR spectrum.

(b) The mixture prepared in accordance with the procedure described in (a) above is mixed with 500 g of anhydrous n-hexane and filtered under dry nitrogen. The substances boiling below bis(vinyldimethylsilyl)carbonate are distilled from the filtrate at a temperature up to 50° C. and at 10 hPa (absolute). About 15.4 g of a clear, yellow oil is obtained from the residue which is identified as bis(vinyldimethylsilyl)carbonate.

EXAMPLE 4

(a) A solution containing 217 g of trimethylchlorosilane in 220 g of dichloromethane (purity: at least 99.5 weight percent CH$_2$Cl$_2$) is added dropwise over 90 minutes with stirring and with the exclusion of water to a flask equipped with an agitator, an addition funnel, thermometer and reflux condenser and containing a mixture consisting of 672 g of sodium bicarbonate (purity: at least 99.5 weight percent $NaHCO_3$), 1780 g of dichloromethane (purity: at least 99.5 weight percent $CH_2Cl_2$) and 966 g of hexamethyldisilazane. After the addition of the silane in the aprotic solvent is complete, stirring is then continued for an additional 45 hours and then filtered under dry nitrogen. The substances boiling below bis(trimethylsilyl)carbonate are distilled from the filtrate at 30° C. and at 10 hPa (absolute). About 370 g of bis(trimethylsilyl)carbonate (90 weight percent of theoretical) is recovered as residue.

What is claimed is:

1. A method for preparing organosilyl carbonates which comprises reacting an organohalosilane with an alkali bicarbonate in the presence of a compound selected from an amine, phosphine and mixtures thereof and an aprotic solvent which is inert to the reactants, separating a halide compound selected from the group consisting of ammonium halide, phosphonium halide and mixtures thereof from the organosilyl carbonate and then removing the organosilyl carbonate from the halide-free mixture.

2. The method of claim 1, wherein the organohalosilane is triorganochlorosilane.

3. The method of claim 2, wherein the triorganochlorosilane is trimethylchlorosilane.

4. The method of claim 2, wherein the triorganochlorosilane is vinyldimethylchlorosilane.

5. The method of claim 1, wherein the alkali bicarbonate is sodium bicarbonate.

6. The method of claim 1, wherein the alkali bicarbonate is present in an amount of from 3 to 5 mols per gram-atom of Si-bonded halogen.

7. The method of claim 1, wherein the amine is selected from the group consisting of hexamethyldisilazane and triethylamine.

8. The method of claim 1, wherein the amine is present in an amount of from 3 to 5 mols per gram-atom of Si-bonded halogen.

9. The method of claim 1, wherein the phosphine is present in an amount of from 3 to 5 mols per gram-atom of Si-bonded halogen.

* * * * *